US009889130B2

(12) United States Patent
Baroni et al.

(10) Patent No.: US 9,889,130 B2
(45) Date of Patent: *Feb. 13, 2018

(54) SUBSTITUTED 3-BENZOFURANYL-INDOL-2-ONE-3-ACETAMIDIDOPIPERAZINE DERIVATIVES, PREPARATION THEREOF, AND THERAPEUTIC USE THEREOF

(71) Applicant: SANOFI, Paris (FR)

(72) Inventors: Marco Baroni, Paris (FR); Letizia Puleo, Paris (FR)

(73) Assignee: SANOFI, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,834

(22) Filed: Nov. 10, 2016

(65) Prior Publication Data

US 2017/0119761 A1 May 4, 2017

Related U.S. Application Data

(63) Continuation of application No. 13/201,141, filed as application No. PCT/FR2010/050206 on Feb. 9, 2010, now abandoned.

(30) Foreign Application Priority Data

Feb. 12, 2009 (FR) ...................... 09 00620

(51) Int. Cl.
*C07D 405/04* (2006.01)
*C07D 405/14* (2006.01)
*A61K 31/496* (2006.01)
*A61K 31/454* (2006.01)

(52) U.S. Cl.
CPC .......... *A61K 31/496* (2013.01); *A61K 31/454* (2013.01); *C07D 405/04* (2013.01); *C07D 405/14* (2013.01)

(58) Field of Classification Search
None
See application file for complete search history.

(56) References Cited

U.S. PATENT DOCUMENTS

| 5,773,612 | A | 6/1998 | Wagnon et al. |
| 7,119,086 | B2 | 10/2006 | Di Malta et al. |
| 8,202,871 | B2 | 6/2012 | Baroni et al. |
| 2011/0312972 | A1 | 12/2011 | Baroni et al. |

FOREIGN PATENT DOCUMENTS

| FR | 2 714 378 A1 | 6/1995 |
| FR | 2 714 378 B1 | 6/1995 |
| WO | WO-95/18105 A1 | 7/1995 |
| WO | WO-03/008407 A2 | 1/2003 |
| WO | WO-03/008407 A3 | 1/2003 |
| WO | WO-2005/035498 A1 | 4/2005 |
| WO | WO-2009/056707 A2 | 5/2009 |
| WO | WO-2010/092288 A1 | 8/2010 |

OTHER PUBLICATIONS

Barazzoni, R. et al. (Dec. 7, 2004; e-published on Aug. 24, 2004). "Ghrelin Regulates Mitochondrial-Lipid Metabolism Gene Expression and Tissue Fat Distribution in Liver and Skeletal Muscle," *American Journal of Physiology Endocrinology and Metabolism* 288(1):E228-E235.

Carpino, P.A et al. (2008; e-published on Oct. 29, 2008). "Modulators of the Ghrelin System as Potential Treatments for Obesity and Diabetes," *Expert Opinion on Therapeutic Patents* 18(11):1253-1263.

Dass, N. B. et al. (Aug. 22, 2003). "Growth Hormone Secretagogue Receptors in Rat and Human Gastrointestinal Tract and the Effects of Ghrelin," *Neurosciences* 120(2):443-453.

Dezaki, K. et al. (Dec. 2004). "Endogenous Ghrelin in Pancreatic Islets Restricts Insulin Release by Attenuating $Ca^{2+}$ Signaling in β-Cells: Implication in the Glycemic Control in Rodents," *Diabetes* 53(12):3142-3151.

Druce, M.R. et al. (Sep. 2005; e-published on May 24, 2005). "Ghrelin Increases Food Intake in Obese as Well as Lean Subjects," *International Journal of Obesity* 29(9):1130-1136.

Kim, M.S. et al. (Oct. 2004; e-published on Jul. 27, 2004). "Chronic Central Administration of Ghrelin Reverses the Effects of Leptin," *Int. J Obes. Relat. Metab. Disord.* 28(10):1264-1271.

Kojima, M. et al. (Dec. 9, 1999). "Ghrelin is a Growth-Hormone-Releasing Acylated Peptide From Stomach," *Nature* 402(6762):656-660.

Prado, C.L. et al. (Mar. 2, 2004). "Ghrelin Cells Replace Insulin-Producing β Cells in Two Mouse Models of Pancreas Development," *Proceedings of the National Academy of Sciences of the United States of America* 101(9):2924-2929.

Soares, J.B. et al. (2008). "Ghrelin abd Ghrelin Receptor Inhibitors: Agents in the Treatment of Obesity," *Expert Opin. Ther. Targets* 12(9):1177-1189.

Sun, Y. et al. (May 2006). "Ablation of Ghrelin Improves the Diabetic But Not Obese Phenotype of Ob/Ob Mice," *Cell Metabolism* 3(5):379-386.

(Continued)

*Primary Examiner* — Emily Bernhardt
(74) *Attorney, Agent, or Firm* — Morrison & Foerster LLP

(57) ABSTRACT

The invention relates to disubstituted 3-benzofuranyl-indol-2-one-3-acetamidopiperazine derivatives of the general formula (I) where R1, R2, R3, R4, R5, R6, R7, R8, R9 and n are such as defined in claim 1, to a method for preparing same, and to the therapeutic use of said compounds.

10 Claims, No Drawings

(56) References Cited

OTHER PUBLICATIONS

Ueno, N. et al. (2004). "Leptin Modulates Orexigenic Effects of Ghrelin and Attenuates Adiponectin and Insulin Levels and Selectively the Dark-Phase Feeding as Revealed by Central Leptin Gene Therapy," *Endocrinology* 145(9):4176-4184.

Wren, A.M. et al. (Dec. 2001). "Ghrelin Enhances Appetite and Increases Food Intake in Humans," *The Journal of Clinical Endocrinology & Metabolism* 86(12):5992-5995.

Wynne, K. et al. (Jul. 2005; e-published on May 11, 2005). "Subcutaneous Ghrelin Enhances Acute Food Intake in Malnourished Patients Who Receive Maintenance Peritoneal Dialysis: A Randomized, Placebo-Controlled Trial," *The Journal of the American Society of Nephrology* 16(7):2111-2118.

International Search Report dated Apr. 22, 2010 issued to PCT/FR2010/050206.

International Preliminary Report on Patentability dated Aug. 16, 2011 issued in PCT/FR2010/050206.

Asakawa, A. et al. (2003). "Antagonism of Ghrelin Receptor Reduces Food Intake and Body Weight Gain in Mice," *Gut* 52:947-952, Exhibit—C.

Broglio, F. et al. (2003). "Endocrine and Non-Endocrine Actions of Ghrelin," *Hormone Research* 59(3):109-117.

Depoortere, I. et al. (May 16, 2005). "Comparison of the Gastroprokinetic Effects of Ghrelin, GHRP-6 and Motilin in Rats in Vivo and in Vitro," *European Journal of Pharmacology* 515(1-3):160-168.

Druce, M.R. et al. (Sep. 2005; e-published on May 24, 2005). "Ghrelin Increases Food Intake in Obese as Well as Lean Subjects," *International Journal of Obesity* 29(9):1130-1136, Exhibit—B.

Ford-Martin, P. (2004). "Sulfonylureas," in *The Everything Diabetes Book*, Avon, Massachusetts: Adams Media Corporation. (p. 110), Exhibit—A.

Fukuda, H. et al. (Dec. 2004). "Ghrelin Enhances Gastric Motility Through Direct Stimulation of Intrinsic Neural Pathways and Capsaicin-Sensitive Afferent Neurones in Rats," *Scandinavian Journal of Gastroenterology* 39(12):1209-1214.

Kenakin, T. (1997). "Competitive Antagonism," Chapter 10 in *Pharmacologic Analysis of Drug-Receptor Interaction*, 3rd edition, Lippincott-Raven Publishers, Philadelphia, New York pp. 331-373.

March, J. ed. (1985). "The Effect of the Leaving Group," Chapter 10 in *Advanced Organic Chemistry*, Third Edition, John Wiley & Sons Inc., pp. 310-316.

Ratkovsky, D.A. et al. (Sep. 1986). "Choosing Near-Linear Parameters in the Four-Parameter Logistic Model for Radioligand and Related Assays," *Biometrics* 42(3):575-582.

Smith, R.G. et al. (Nov. 2005). "Developments in Ghrelin Biology and Potential Clinical Relevance," *Trends in Endocrinology and Metabolism* 16(9):436-442.

Wuts, P.G.M and Greene, W. ed. et al. (2007). *Green's Protective Groups in Organic Synthesis*, 4th edition (John Wiley & Sons, Inc., New York), Table of Contents, twenty seven pages.

Wuts, P.G.M and Greene, W. eds. (2007). "The Role of Protective Groups in Organic Synthesis," Chapter 1 in *Green's Protective Groups in Organic Synthesis*, Greene et al., 4th edition, John Wiley & Sons, Inc., New York, pp. 1-15.

Wuts, P.G.M and Greene, W. eds. (2007). "Protection for the Hydroxyl Group," Including 1,2- and 1,3-Diols, Chapter 2 in *Green's Protective Groups in Organic Synthesis*, Greene et al., 4th edition, John Wiley & Sons, Inc., New York, pp. 16-366.

Wuts, P.G.M and Greene, W. eds. (2007). "Protection for Phenols and Catechols," Chapter 3 in *Green's Protective Groups in Organic Synthesis*, Greene et al., 4th edition, John Wiley & Sons, Inc., New York, pp. 367-430.

Wuts, P.G.M and Greene, W. eds. (2007). "Protection for the Carbonyl Group," Chapter 4 in *Green's Protective Groups in Organic Synthesis*, Greene et al., 4th edition, John Wiley & Sons, Inc., New York, pp. 431-532.

Wuts, P.G.M and Greene, W. eds. (2007). "Protection for the Carboxyl Group," Chapter 5 in *Green's Protective Groups in Organic Synthesis*, Greene et al., 4th edition, John Wiley & Sons, Inc., New York, pp. 533-646.

Wuts, P.G.M and Greene, W. eds. (2007). "Protection for the Thiol Group," Chapter 6 in *Green's Protective Groups in Organic Synthesis*, Greene et al., 4th edition, John Wiley & Sons, Inc., New York, pp. 647-695.

Wuts, P.G.M and Greene, W. eds. (2007). "Protection for the Amino Group," Chapter 7 in *Green's Protective Groups in Organic Synthesis*, Greene et al., 4th edition, John Wiley & Sons, Inc., New York, pp. 696-926.

Wuts, P.G.M and Greene, W. eds. (2007). "Protection for the Alkyne-CH," Chapter 8 in *Green's Protective Groups in Organic Synthesis*, Greene et al., 4th edition, John Wiley & Sons, Inc., New York, pp. 927-933.

Wuts, P.G.M and Greene, W. eds. (2007). "Protection for the Phosphate Group," Chapter 9 in *Green's Protective Groups in Organic Synthesis*, Greene et al., 4th edition, John Wiley & Sons, Inc., New York, pp. 934-985.

Wuts, P.G.M and Greene, W. eds. (2007). "Reactivities, Reagents, and Reactivity Charts," Chapter 10 in *Green's Protective Groups in Organic Synthesis*, Greene et al., 4th edition, John Wiley & Sons, Inc., New York, pp. 986-1051.

Wuts, P.G.M and Greene, W. ed. et al. (2007). *Green's Protective Groups in Organic Synthesis*, 4th edition (John Wiley & Sons, Inc., New York), Index, pp. 1053-1082.

SUBSTITUTED 3-BENZOFURANYL-INDOL-2-ONE-3-ACETAMIDIDOPIPERAZINE DERIVATIVES, PREPARATION THEREOF, AND THERAPEUTIC USE THEREOF

This application is a continuation of U.S. patent application Ser. No. 13/201,141, filed Aug. 11, 2011, which is a National Phase application under 35 U.S.C. § 371 of International Application No. PCT/FR2010/050206, filed Feb. 9, 2010, which claims priority and benefit of FR Application No. 09/00620, filed Feb. 12, 2009, the disclosures of each of which are incorporated herein by reference in their entirety.

The present invention relates to substituted 3-benzofuranyl-indol-2-one-3-acetamidopiperazine derivatives, to their preparation and to their therapeutic application.

Ghrelin is a 28 amino-acid peptide hormone produced mainly in the stomach by a post-transitional process after cleavage of pre-pro-ghrelin (Kojima M., et al., *Nature* 1990; 402: 656-60). Ghrelin is an endogenous ligand of the growth hormone secretagogue pituitary receptor (GHSR1a).

GHS-R is encoded by two exons: exon 1 encodes the transmembrane domains (TMs) 1-5 and exon 2 encodes TM6 and 7 of the G-protein-coupled receptor (GPCR).

The two transcripts have been identified in the pituitary gland and the brain: one encoding the full-length GPCR (GHS-R1a) and the other encoding a truncated receptor (GHS-R1b) lacking TM6 and 7. Only the subtype GHS-R1a is activated by ghrelin and ghrelin mimetics. GHS-R1b is present in the liver and other peripheral tissues, but its function is unknown (Smith R. G, et al., *Trends in Endocrinology and Metabolism*, 2005, 16, No. 9).

It is a receptor of rhodopsin type, with seven transmembrane domains of family A coupled to Gq/phospholipase C. The ghrelin receptor may also be coupled to the Gs/protein kinase A pathways in certain tissues (Ueno, M. et al., *Endicrinology*, 2004, 145, 4176-4184; Kim, M. S. et al., *Int. J. Obes. Relat. Metab. Disord.*, 2004, 28: 1264-1271). Interestingly, the ghrelin receptor has the relatively uncommon characteristic of having significant ligand-independent constitutive activity (Barazzoni, R. et al. *Am. J. Physiol. Endocrinol. Metab.*, 2004, 268: E228-E235).

Low levels of expression of ghrelin have been documented in various tissues, such as the intestines, the pancreas, the kidneys, the immune system, the placenta, the testicles, pituitary tissue and the hypothalamus (*Horm. Res.* 2003; 59 (3): 109-17).

It has been demonstrated that ghrelin is involved in hunger at mealtimes and in the initiation of meals. The circulating levels decreases with the intake of food and increase after meals, reaching concentrations that are sufficient to stimulate hunger and the intake of food ingestion of ghrelin stimulates food intake rapidly and transiently, mainly by increasing the appetitive feeding behaviour and the number of meals. Ghrelin stimulates the short-term taking of food more efficiently than any other molecule, with the exception of neuropeptide Y, with which it is approximately equipotent (Wren A. M. et al., *J. Clin. Endocrinol. Metab.* 2001; 86: 5992-5). However, ghrelin is unique in its capacity to exert this effect, whether it is injected peripherally or centrally.

It is also the only mammalian substance that has demonstrated its capacity to increase the appetite and the taking of food when if is administered to humans (Druce M. R., et al., *Int. J. Obes.*, 2005; 29: 1130-6; Wynne K., et al., *J. Am. Soc. Nephrol.* 2005; 16: 2111-8).

Beyond its role in the initiation of meals, ghrelin also satisfies the established criteria of an adiposity-related hormone involved in regulating the long-term body mass. The levels of ghrelin circulate as a function of the energy reserves and display compensatory changes in response to changes in body mass.

Ghrelin crosses the blood-brain barrier and stimulates the taking of food by acting on certain standard body mass-regulating centres, such as the hypothalamus, the hindbrain and the mesolimbic compensatory system.

Chronic administration of ghrelin increases the body mass via diverse concerted actions on the taking of food, energy expenditure and the utilisation of resources. Congenital ablation of ghrelin or of the ghrelin receptor gene causes a resistance to feeding-induced obesity, and pharmacological blocking of ghrelin reduces the intake of food and the body mass.

The existing evidence appears to favour the rote of ghrelin both in the short-term initiation of meals and long-term energy homeostasis, thus making it an attractive target as a medicament for treating obesity and/or slimming disorders.

Ghrelin also exerts both physiological and pharmacological actions on the endocrine pancreas. Acylated bioactive ghrelin is produced in the ε cells, recently described in the pancreatic islets (Prado, C. L., et al., 2004, *Proc. Natl Acad. Sci. USA*, 101: 2924-2929), potentially providing a local source of ghrelin that acts on the β cells of the islets. Blockage of this function of endogenous ghrelin by means of an antagonist for its receptors substantially reduced the fasted glucose concentrations attenuated the glycaemic movement and increased the responses to insulin during glucose tolerance tests, suggesting an inhibitory role of ghrelin in the control of insulin secretion (Dezaki, K., et al. 2004, *Diabetes*, 53: 3142-3151).

Ablation of ghrelin in mice (ghrelin–/–mice) increases the glucose-dependent secretion of insulin by the β cells of the pancreas, by reducing the Ucp2 expression and increases the sensitivity to peripheral insulin (Sun Y. et al., 2006, *Cell Metabolism*, 3: 379-386).

Ghrelin receptor antagonists could thus regulate hunger, the taking of meals and their frequency, and also, in the long-term, the weight, especially weight gain following diets or therapeutic regimens. Furthermore, in the context of an antidiabetic treatment, ghrelin antagonists could be useful for maintaining the equilibrium between insulin and glucose for controlling diabetic hyperphagia. Ghrelin antagonists could thus be used as anorexic and/or anti-obesity agents, or alternatively in the treatment of diabetes and its affects.

One subject of the present invention is compounds corresponding to formula (I):

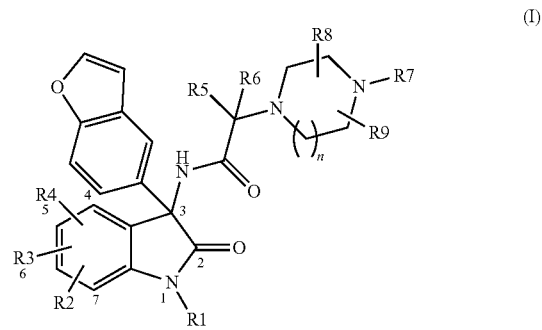

in which:
R1 represents a hydrogen atom or a (C1-6)alkyl, —C(═O)(C1-6)alkyl or —C(═O)aryl group;

R2, R3 and R4, which may be identical or different located on any of the available positions of the phenyl nucleus, independently represent a hydrogen atom, a halogen atom, CN, OH, a (C1-6)alkyl group optionally substituted with a halogen atom or an OH; perhalo(C1-3)alkyl, (C1-6)alkoxy, perhalo(C1-3)alkoxy, aminocarbonyl, (C1-6)alkylaminocarbonyl, di(C1-6)alkylaminocarbonyl, aryl, aryloxy; heteroaryl; the aryl, aryloxy or heteroaryl group possibly being optionally substituted with a halogen atom, CN, OH or a (C1-8)alkyl, perhalo(C1-3)alkyl or (C1-6)alkoxy group; if being understood that at least one from among R2, R3 and R4 is other than H and that the aryl, aryloxy or heteroaryl group may be optionally substituted with a halogen atom, CN, OH or a (C1-6)alkyl, perhalo(C1-3)alkyl or (C1-6) alkoxy group;

R5 and R6, which may be identical or different, represent a hydrogen atom or a group (C1-6)alkyl or R5 and R6 together form a C3-C6 ring;

R7 represents a group (C1-C6)alkyl or a group (C2-8) alkenyl;

R8 and R9, which are located on any of the available positions of the piperazine nucleus, represent a hydrogen atom, a group (C1-C6)alkyl or a group (C2-6)alkenyl it being understood that at least one from among R8 and R9 is other than H;

or two from among R7, R8 and R9 together form a C3-C8 ring;

it being understood that R8 and R9 may be in the geminal position on the same carbon atom;

n represents 1 or 2.

The compounds of formula (I) comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts may be prepared with pharmaceutically acceptable acids, but the salts of other acids that are useful for example, for purifying or isolating the compounds of formula (I) also form part of the invention.

In the context of the present invention, the following definitions apply:

a halogen atom: a fluorine, a chlorine, a bromine or an iodine;

an alkyl group: a linear or branched saturated aliphatic group. Examples that may be mentioned include a (C1-6)alkyl group containing from 1 to 6 carbon atoms, more particularly (C1-4)alkyl, which may represent a methyl, ethyl, propyl, isopropyl, butyl, isobutyl or tert-butyl;

an alkenyl a linear or branched, monounsaturated or polyunsaturated aliphatic group comprising, for example, one or two unsaturations and containing from 2 to 8 carbon atoms;

a haloalkyl group: an alkyl group in which one or more hydrogen atoms have been replaced with a halogen atom; for example a fluoroalkyl; an alkyl group in which one or more hydrogen atoms have been replaced with a fluorine atom;

a perhaloalkyl group: an alkyl group in which all the hydrogen atoms have been replaced with a halogen atom, for example, a perfluoroalkyl, an alkyl group in which all the hydrogen atoms have been replaced with a fluorine atom;

an alkoxy group: a radical —O-alkyl in which the alkyl group is as defined above;

a perhaloalkoxy group: a radical —O-perhaloalkyl in which the perhaloalkyl group is as defined above; mention may be made, for example, of trifluoromethoxy;

an aryl group: a cyclic aromatic group containing between 8 and 10 carbon atoms. Examples of aryl groups that may be mentioned include phenyl and naphthyl;

a heteroaryl group: a cyclic aromatic group containing between 2 and 10 carbon atoms and comprising between 1 and 3 heteroatoms, such as nitrogen, oxygen or sulfur. Examples of heteroaryl groups that may be mentioned include furyl, pyrrolyl, imidazolyl, pyrazolyl, thienyl, oxadiazolyl, oxazoyl, isoxazolyl, furazanyl, thiadiazolyl, thiazolyl, isothiazolyl, pyridyl, pyrazinyl, pyrimidinyl and pyridazinyl groups, and also the corresponding groups resulting from fusion with a phenyl group, for instance benzothiophene, benzofuran, benzothiazole, etc.

Among the compounds of formula (I) that are subjects of the invention, one group of compounds is constituted by the compounds for which:

R1 represents a hydrogen atom or a (C1-6)alkyl, —C(=O) (C1-6)alkyl or —C(=)aryl group;

R2, R3 and R4 which may be identical or different, located on any of the available positions of the phenyl nucleus. Independently represent a hydrogen atom, a halogen atom, CN, OH or a (C1-6)alkyl perhalo(C1-3)alkyl, (C1-6)alkoxy perhalo(C1-3)alkoxy, aminocarbonyl, (C1-6)alkylaminocarbonyl, di(C1-6)alkylaminocarbonyl, aryl, aryloxy or heteroaryl group, it being understood that at least one from among R2, R3 and R4 is other than H;

R5 and R6 which may be identical or different represent a hydrogen atom a group (C1-6)alkyl or R5 and R6 together form a C3-C6 ring;

R7 represents a group (C1-C6)alkyl;

R8 and R9, which are located on any of the available positions of the piperazine nucleus, represent a hydrogen atom, a group (C1-C6)alkyl, it being understood that at least one from among R8 and R9 is other than H;

or two from among R7, R8 and R9 together form a C3-C6 ring;

n represents 1 or 2;

in the form of the base or of an acid-addition salt.

Among the compounds of formula (I) that are subjects of the invention, one group of compounds is constituted by the compounds for which:
R1 represents a hydrogen atom or a —C(=O)(C1-6)alkyl, —C(=O)aryl or (C1-6)alkyl group; and/or
R2, R3 and R4, which may be identical or different, located on any of the available positions of the phenyl nucleus, independently represent a hydrogen atom, a halogen atom, more particularly chlorine or bromine, or a (C1-6)alkyl or trifluromethyl group, it being understood that at least one from among R2, R3 and R4 is other than H; and/or
R5 and R6 which way be identical or different, represent a hydrogen atom or a group (C1-6)alkyl; and/or
R7 represents a group (C1-C6)alkyl; and/or
R8 and R9, which are located on positions 2 and 6 of the piperazine nucleus, represent a hydrogen atom, a group (C1-C6)alkyl, it being understood that at least one from among R8 and R9 is other than H; and/or
two from among R7, R8 and R9 together form a C3-C6 ring; and/or
n represents 1 or 2;
in the form of the base or of an acid-addition salt.

Among the compounds of formula (I) that ere subjects of the invention, another group of compounds is constituted by the compounds for which:
R1 represents a hydrogen atom or a —C(=O)methyl, —C(=O)phenyl or methyl group; and/or
R2, R3 and R4, which may be identical or different, located on any of the available positions of the phenyl nucleus, independently represent a hydrogen atom, a halogen atom, more particularly chlorine or bromine, or a methyl or trifluoromethyl group, it being understood that at least one from among R2, R3 and R4 is other than H; and/or
R5 and R6, which may be identical or different, represent a hydrogen atom or a group (C1-6)alkyl; and/or
R7 represents a methyl or ethyl group; and/or
R8 and R9, which are located on positions 2 and 6 of the piperazine nucleus, represent a hydrogen atom or a methyl or ethyl group, it being understood that at least one from among R8 and R9 is other than H; and/or
two from among R7, R8 and R9 together form a C3-C8 ring; and/or
n represents 1 or 2;
in the form of the base or of an acid-addition salt.

Among the compounds of formula (I) that are subjects of the Invention, mention may be made especially of the following compounds:
Compound No. 1: (+)-N-[4,6-dichloro-3-(benzofuran-5-yl)-2-oxo-2,3-dihydro-1H-indol-3-yl]-2-(4-ethyl-3,5-dimethylpiperazin-1-yl)acetamide;
Compound No. 2: (+)-N-[4,6-dichloro-3-(benzofuran-5-yl)-2-oxo-2,3-dihydro-1H-indol-3-yl]-2-(4-ethylpiperazin-1-yl)propionamide;
in the form of the base or of an acid-addition salt.

In the text hereinbelow, the term "protecting group Pg" means a group that makes it possible firstly to protect a reactive function such as a hydroxyl or an amine during a synthesis, and, secondly, to regenerate the intact reactive function at the end of the synthesis. Examples of protecting groups and of protection and deprotection methods are given in *Protective Groups in Organic Synthesis*, Greene et al., 2nd edition (John Wiley & Sons. Inc., New York).

In the text hereinbelow, the term "leaving group" means a group that may be readily cleaved from a molecule by creaking a heterolytic bond, with loss of an electron pair. This group may thus be readily replaced with another group during a substitution reaction, for example. Such leaving groups are, for example, halogens or an activated hydroxyl group such as a methanesulfonate, benzenesulfonate, p-toluenesulfonate, triflate, acetate, etc. group. Examples of leaving groups and references for their preparation are given in *Advances in Organic Chemistry*, J. March, 3rd edition, Wiley Interscience, pp. 310-316.

In accordance with the invention, the compounds of general formula (I) may be prepared according to the process that follows:

Scheme 1:

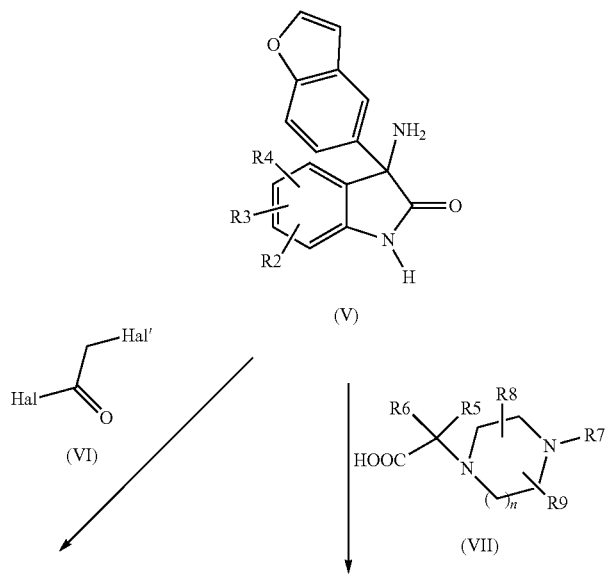

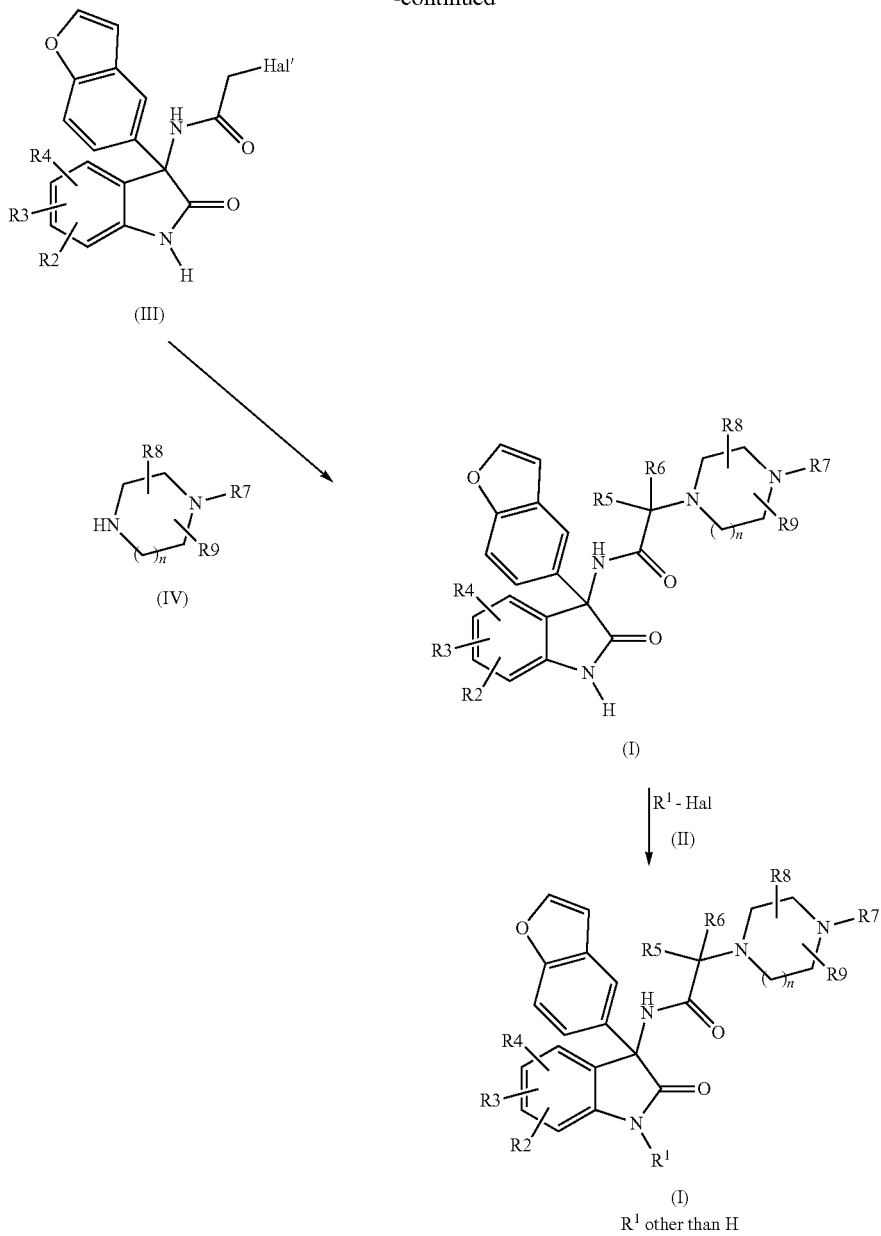

The compound of formula (I), in which R1 is other than H and R2, R3, R4, R5, R6, R7, R8, R9 and n are as defined in the general formula (I), may be prepared by reacting a compound of formula (I) in which R1=H with a compound of formula (II):

R1-Hal  (II)

in which R1, which is ether than H, is defined as in the general formula (I) and Hal represents a halogen atom, for example chlorine, according to methods known to those skilled in the art, for example in the presence of a base such as $K_2CO_3$, NaH or t-BuO$^-$K$^+$, in a solvent such as dimethylformamide (DMF), tetrahydrofuran (THF), dimethoxyethane or dimethyl sulfoxide (DMSO).

The compound of general formula (I) may be prepared according to one or other of the following variants:

The compound of general formula (I) in which R1=H may be prepared according to the following method, from a compound of general formula (V):

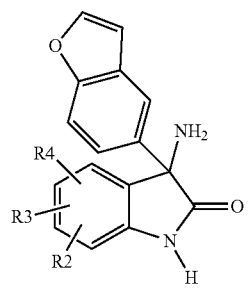

and from a compound of general formula (VII):

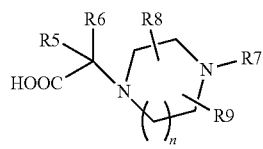

(VII)

in which R2, R3, R4, R5, R6, R7, R8, R9 and n are as defined in the general formula (I). This reaction is generally performed using a halogenating agent, such as a chlorinating agent, for example phosphorus chlorides, especially PCl$_5$, or alternatively PCl$_3$ or POCl$_3$. The reaction is generally performed in the presence of pyridine or 4-dimethylaminopyridine, in a solvent such as dichloromethane or DMF.

The compound of general formula (I) in which R1, R5 and R6=H may be prepared according to the following method, by reacting a compound of general formula (III):

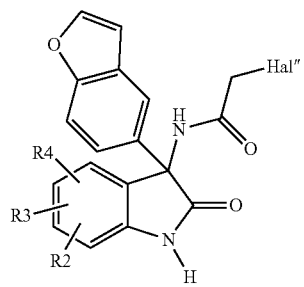

(III)

with a compound of general formula (IV):

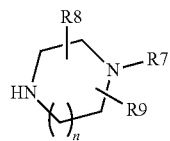

(IV)

in which R2, R3, R4, R7, R8, R9 and n are as defined in the general formula (I) and Hal" represents a Halogen atom, preferably chlorine. This reaction is generally performed using an organic or mineral base, such as K$_2$CO$_3$, N$_2$CO$_3$, pyridine or 4-dimethylaminopyridine in the presence of NaI or KI, in an inert solvent such as DMF, dichloromethane, THF, dimethoxyethane or toluene.

The compound of general formula (III) may be prepared from a compound of general formula (V):

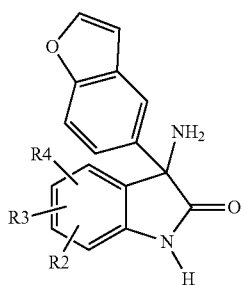

(V)

and from a compound of general formula (VI):

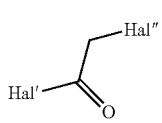

(VI)

in which R2, R3 and R4 are as defined in the general formula (I) and Hal' and Hal", which may foe identical or different independently represent a halogen atom, preferably chlorine.

This reaction is generally performed using pyridine or 4-dimethylaminopyridine in a solvent such as toluene, benzene or dichloromethane, preferentially at a temperature of between room temperature and the reflux point of the solvent.

Room temperature is meant to be a temperature of between 5 and 25° C.

The intermediates of general formula (V) are known and may be prepared according to the processes illustrated by scheme that follows:

Scheme 2:

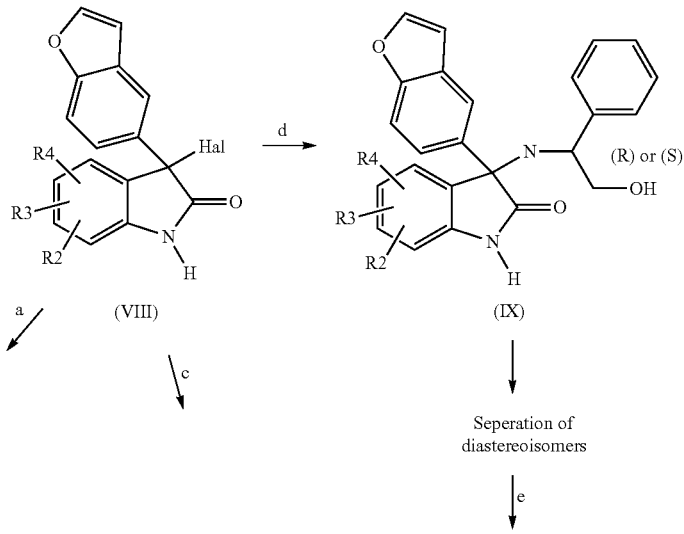

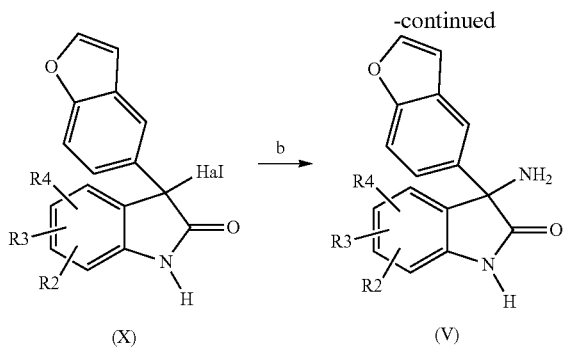

in which R2, R3 and R4 are as defined in the general formula (I) and Hal represents a halogen atom, for example chlorine.

In step c of Scheme 2, the compound of formula (V) is prepared from a compound of formula (VIII) by sparging with ammonia gas according to the method described in patent application FR 2 714 378.

It is also possible to prepare the same compound via reduction of a compound of formula (X) according to methods known to those skilled in the art, for example by means of zinc in a solvent such as methanol. The preparation of a compound of formula (X) of the step is described in patent application FR 2 714 378.

An optically pure compound of formula (V) may be synthesized according to steps d and e of Scheme 2, as described in patent application WO 03/008407.

The intermediates of general formula (VIII) may be prepared according to the processes described in patent application WO 03/008407 and illustrated by Scheme 3:

Scheme 3:

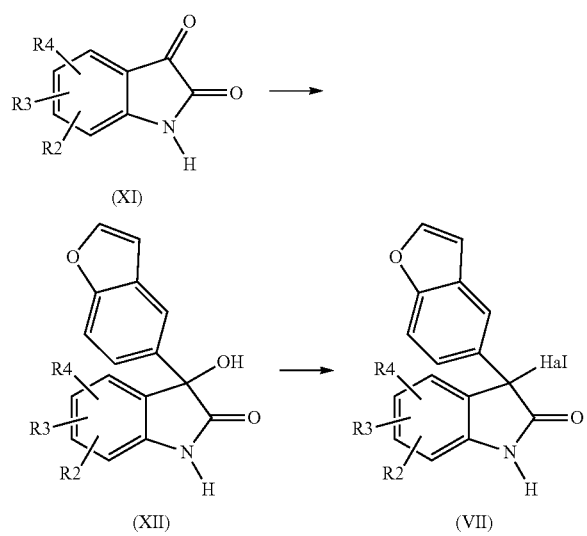

in which R2, R3 and R4 are as defined in the general formula (I) and Hal represents a halogen atom, for example chlorine.

The compound of general formula (VII) may be prepared according to the following methods, illustrated by Schemes 4 and 5:

Scheme 4:

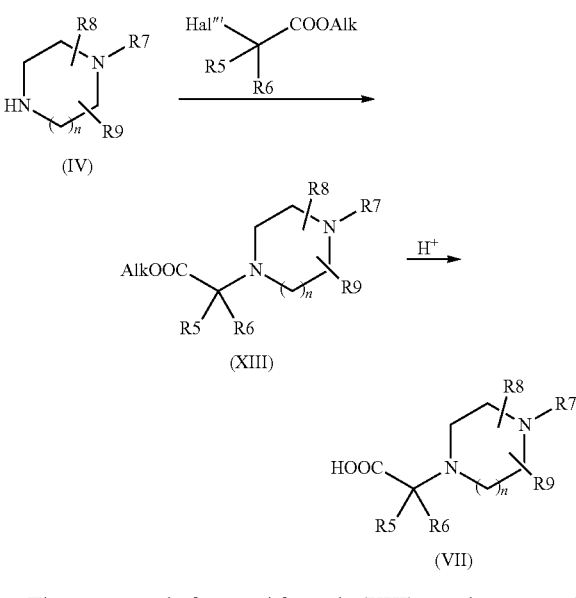

The compound of general formula (XIII) may be prepared by condensation of compound of general formula (IV):

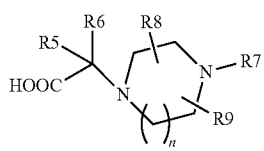

(VII)

in which R7, R8, R9 and n are defined as in the general formula (I), with a corresponding halo compound such as Hal'''CH$_2$COOAlk, in which Hal''' represents a halogen atom such as chlorine and Alk represents an alkyl group, such as ethyl. This reaction is advantageously performed in a solvent such as toluene, benzene or dioxane.

Scheme 5:

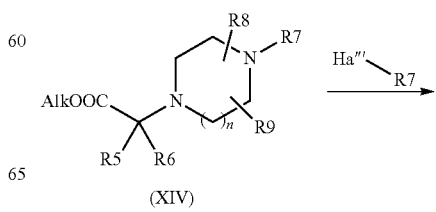

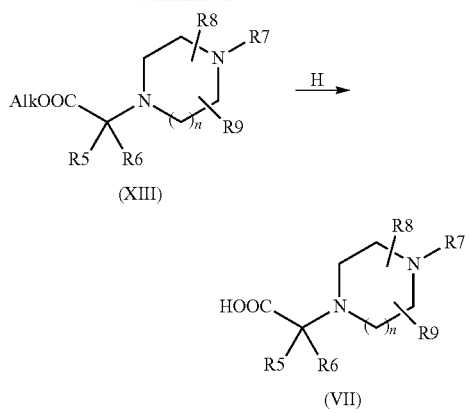

The compound of general formula (XII) may be prepared by condensation of a compound of general formula (XIV):

in which R5, R6, R8, R9 and n are defined as in the general formula (I) and Alk represents an alkyl group, with a compound R7-Hal''' in which Hal''' represents a halogen atom, such as chlorine, and R7 is defined as in the general formula (I). This reaction is advantageously performed in a solvent such as toluene, benzene, dioxane or DMF in the presence of a base such as triethylamine or potassium carbonate.

According to another embodiment, the compounds of general formula (I) in which R1 represents an alkyl group and R2, R3, R4, R5, R6, R7, R8, R9 and n are as defined in the general formula (I) may also be prepared according to Scheme 8 below:

Scheme 6:

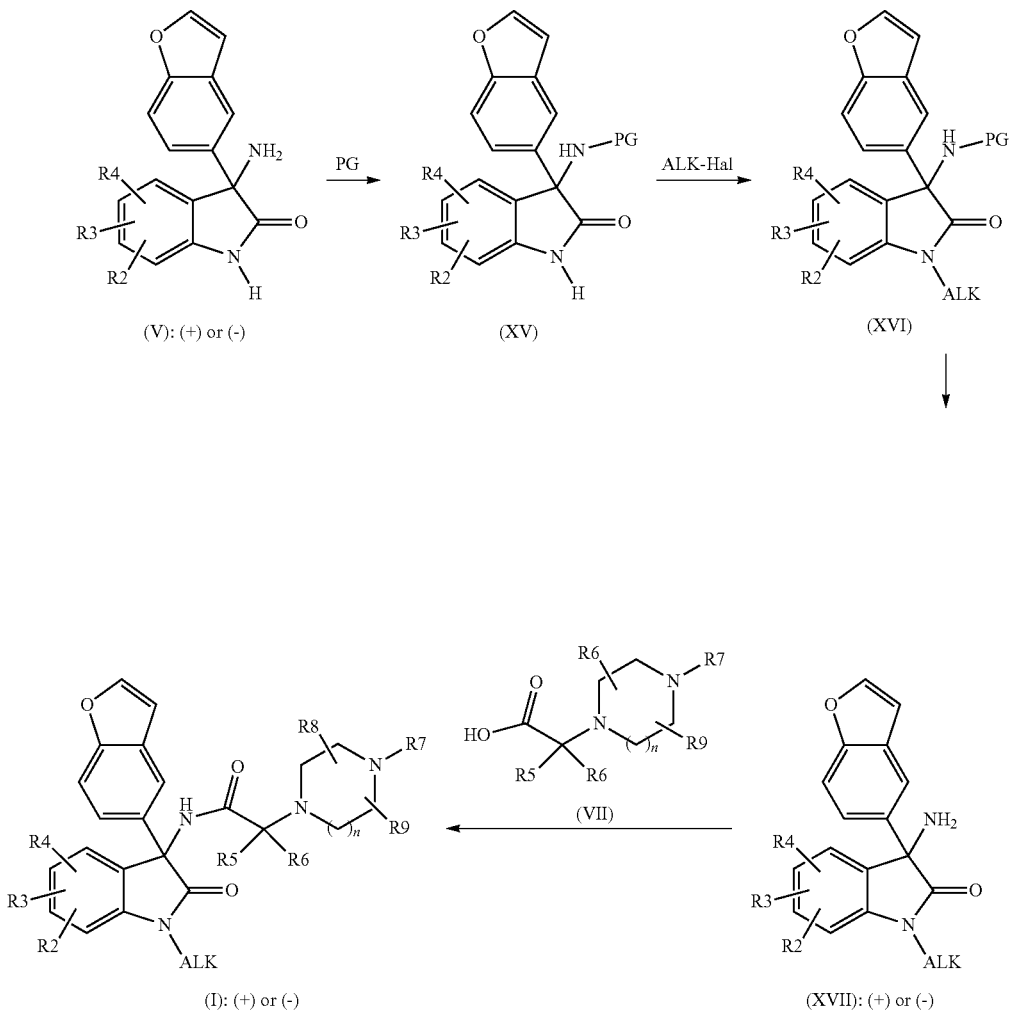

According to this scheme, a compound of formula (V) is reacted with a protecting group PG to give the compound of formula (XV). Examples of protecting groups PG for the amine that may be used include benzimine and t-butyl carbamate. These protecting groups are introduced according to methods known to those skilled in the art, for example in the presence of a base such as K$_2$CO$_3$, NaOH or triethylamine, in a solvent such as dioxane, THF or DMSO.

The compound of general formula (XVI) may be prepared by reacting a compound of formula (XV) with a compound of formula ALK-Hal which ALK represents a linear or branched saturated aliphatic group containing from 1 to 6 carbon atoms and Hal represents a halogen atom, for example chlorine.

The compound of general formula (XVII) is obtained from a compound of formula (XVI) by removing the protecting group according to well-known methods, for example in acidic medium with HCl or trifluoroacetic acid.

The compound of formula (XVII) obtained is then reacted with a compound of general formula (VII):

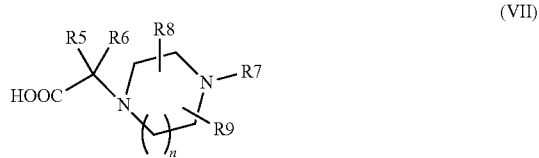

(VII)

in which R2, R3, R4, R5, R6, R7, R8, R9 and n are as defined in the general formula (I). This reaction is generally performed using a halogenating agent such as a chlorinating agent, for example phosphorus chlorides, especially PCl$_5$ or PCl$_3$ or POCl$_3$. The reaction is generally performed in the presence of pyridine or 4-dimethylaminopyridine, in a solvent such as dichloromethane or DMF.

Optionally, the compound of formula (I) is converted into an acid-addition salt thereof.

The process according to the invention may optionally include the step that consists in isolating the desired product of general formula (I).

In Schemes 1, 2, 3, 4, 5 and 6, the starting materials and the reagents, when their mode of preparation is not described, are commercially available or described in the literature, or else may be prepared according to methods that are described therein or that are known to those skilled in the art.

The examples that follow describe the preparation of certain compound in accordance with the invention. These examples are not limiting, and serve merely to illustrate the present invention.

The physiochemical measurements were performed in the following manner.

The melting points were measured using a Büchi B-540 machine.

The proton nuclear magnetic resonance ($^1$H NMR) spectra were recorded at 500 MHz on a Brüker machine equipped with an Avance console. The chemical shifts are given in ppm relative to the frequency of TMS.

All the spectra were recorded at a temperature of 40° C.
The abbreviations used to characterized the signals are as follows:
s=singlet, bs=broad singlet, m=multiplet, bm=broad multiplet, d=doublet, bd=broad doublet, t=triplet, q=quartet.
*=not integratable due to interference with a broad peak resulting from water.
**=not integratable due to interference with a peak resulting from the NMR solvent.
***=read at first order.
****=the most abundant diastereoisomer.
******=the least abundant diastereoisomer.

The analysis conditions by chromatography coupled to mass spectrometry (LC/UV/MS) are as follows:
For the liquid chromatography part:
XTerra MS C18 3.5 µm column
chromatographic system:
Eluent A=H$_2$O+0.01% TFA
Eluent B=CH$_3$CN
gradient from 98% A to 95% 8 over 10 minutes, followed by elusion with 95% B for 5 minutes
flow rate 0.5 ml/minute
injection of 2 µL of solution at 0.1 mg/ml in a 9/1 CH$_3$CN/H$_2$O mixture
The products are detected by UV at 220 nm.
For the mass spectrometry part:
ionization mode: positive electrospray (API-ES polarity+) scanning from 100 to 1200 amu.

Thin layer chromatography was performed on silica gel TLC plates from Merck. The silica gel for the flash column chromatography is sold by Biotage.

All the solvents used are of "reagent grade" or "HPLC grade" purity.

The α$_D$ measurements were recorded on a Perkin-Elmer model PE341 polarimeter using a cell with a 1 dm optical path length.

In the examples and preparations:
AcOH and EtOAc represent, respectively, acetic acid and ethyl acetate.
MeOH, EtOH and t-BuOH represent, respectively, methanol, ethanol and tert-butanol.
THF represents tetrahydrofuran.
m.p. means melting point.

Preparation 1

2-(4-Ethylpiperazin-1-yl)propionic acid (i) Ethyl-2-(4-ethylpiperazin-1-yl)propionate 9.7 g of ethyl 2-piperazin-1-ylpropionate are placed in 150 ml of DMF and 21.6 g of potassium carbonate in a round-bottomed flask. A solution of 3.9 ml of bromoethane is added dropwise. The mixture is reacted at 130° C. for three hours, the carbonate is filtered off and the filtrate is concentrated to dryness. The residue is taken up in ethyl acetate and filtered. The solid is removed and the liquid phase is evaporated under vacuum. A solid that crystallizes from ethyl acetate is obtained. It is filtered off to give 8.46 g of the title product.
TLC: 100% MeOH, Rf=0.55.

(ii) 2-(4-Ethylpiperazin-1-yl)propionic acid 8.45 g of the product obtained in the preceding step are added to 180 ml of 6N HCl and the mixture is reacted for 4 hours at reflux. The resulting mixture is evaporated to dryness, the residue is washed with a 1/1 EtOAc/EtOH mixture and the white solid obtained is dried. 5.4 g of expected product are obtained.

TLC: 100% MeOH, Rf=0.2

Preparation 2

(+)-3-Amino-4,6-dichloro-1,3-dihydro-3-(benzofuran-5-yl)indole-2-one (i) 3-Hydroxy-4,6-dichloro-1,3-dihydro-3-(benzofuran-5-yl)indole-2-one 2.25 g of magnesium for a Grignard reaction in 15 ml of anhydrous THF are pieced on a round-bottomed flask equipped with a mechanical stirrer, and under a stream of nitrogen. A mixture of 13.6 g of 5-bromobenzofuran in 35 ml of anhydrous THF is then added. The mixture is stirred for one hour, followed by addition of a solution of 5 g of 4,6-dichloro-indole-2,3-dione in 50 ml of anhydrous THF. The mixture is stirred at room temperature for 4 hours 30 minutes. Water is added and the resulting mixture is extracted with ethyl acetate. The organic phase is separated out, dried over $Na_2SO_4$, filtered and evaporated under vacuum. The residue is taken up in ethyl acetate and washed with 1N sodium hydroxide solution. The organic phase is dried over $Na_2SO_4$, filtered and evaporated under vacuum. The solid is taken up in ethyl ether and filtered off. 4.2 g of expected product are obtained.

(ii) 3,4,6-Tichloro-1,3-dihydro-3-benzofuran-5-yl)indole-2-one 4.1 g of the product from the preceding step are placed in 40 ml of dichloromethane in a round-bottomed flask equipped with a magnetic stirrer, and under a stream of nitrogen. At 0° C., 1.7 ml of pyridine and a mixture of 1.4 ml of $SOCl_2$ in 30 ml of dichloromethane are added. The resulting mixture is reacted at room temperature and then poured into saturated aqueous $NH_4Cl$ solution. The organic phase is separated out, dried over $Na_2SO_4$, filtered and evaporated under vacuum.
TLC: 7/3 hexane/EtOAc, Rf=0.65

(iii) 4,6-Dichloro-[[(1S)-2-hydroxy-1-phenylethyl]amino]-1,3-dihydro-3-(benzofuran-5-yl)indole-2-one Isomer A and Isomer B 4.1 g of the compound from the preceding step in 50 ml of dichloromethane and 3.1 g of S-phenylglycinol are mixed together under a stream of nitrogen. The mixture is left to react overnight at room temperature. The solid formed is filtered off and the nitration liquors are evaporated to dryness and purified on a column, eluting with 8/2 hexane/EtOAc.
0.64 g of less polar product, isomer A (m.p.=135° C.) and 1.23 g of the more polar isomer B are obtained.

(v) (+)-3-Amino-5,6-dichloro-1,3-dihydro-3-(4-chlorophenyl)indole-2-one 1.21 g of the product obtained in the preceding step in a mixture of 20 ml of dichloromethane and 15 ml of methanol are reacted. 1.26 g of $Pb(OAc)_4$ are added and the mixture is reacted at mom temperature for 1 hour. The resulting mixture is evaporated to dryness and the residue is taken up in ethyl acetate and then washed with saturated aqueous $NaHCO_3$ solution. The organic phase is dried, filtered end concentrated. The residue is taken up in a mixture of 36 ml of 3N hydrochloric add and 3.7 ml of methanol and stirred overnight. The resulting mixture is concentrated and the residue is diluted with a mixture of wafer and dichloromethane. The organic phase is washed with 1N hydrochloric acid solution. The aqueous phases are combined brought to basic pH with aqueous $NH_3$ solution and extracted with dichloromethane. The organic phase is dried, filtered and concentrated to give 870 mg of solid white product.
m.p.=215-216° C.
LC/MS: $(M+H)^+$=m/z 333 amu, rt=5.3 minutes

EXAMPLE 1

(+)-N-[4,6-Dichloro-3-(benzofuran-5-yl)-2-oxo-2,3-dihydro-1H-indol-3-yl]-2-(4-ethyl-3,5-dimethylpiperazin-1-yl)acetamide (i) 2-Chloro-N-[4,6-dichloro-3-(benzofuran-5-yl)-2-oxo-2,3-dihydro-1H-indol-3-yl]acetamide 0.43 g of the product obtained in Preparation 2, 15 ml of toluene, 0.11 ml of pyridine and 0.11 ml of chloroacetyl chloride are placed in a round-bottomed flask equipped with a magnetic stirrer, and under a stream of nitrogen. The mixture is reacted at 110° C. for 4 hours and the reaction mixture is then poured into water and extracted with ethyl acetate. The organic phase is dried over $Na_2SO_4$, filtered and evaporated under vacuum 500 mg of a beige-coloured solid are obtained, which product is purified on a column by flash chromatography using an 8/2 cyclohexane/ethyl acetate mixture to obtain 330 mg of the expected product.
TLC: 1/1 hexane/EtOAc, Rf=0.5

(ii) (+)-N-[4,6-Dichloro-3-(benzofuran-2-yl)-2-oxo-2,3-dihydro-1H-indol-3-yl]-2-(3,5-dimethyl-4-ethyl-piperazin-1-yl)acetamide 0.31 g of the product from the preceding step, 0.08 ml of 2,6-dimethyl-N-ethylpiperazine (d 0.899), 0.1 g of potassium carbonate and 0.05 g of sodium iodide in 5 ml of DMF are placed in a round-bottomed flask equipped with a magnetic stirrer. The mixture is reacted at 60° C. for 4 hours and the reaction mixture is then poured into water and extracted with ethyl acetate. The organic phase is dried over $Na_2SO_4$, filtered and evaporated under vacuum. The title product is obtained.
m.p.=157-160° C.; $[\alpha_D]$, c=0, 946 wt % MeOH;
LC/MS: $(M+H)^+$=m/z 515 amu; rt=4.9 minutes

EXAMPLE 2

(+)-N-[4,6-Dichloro-3-(benzofuran-5-yl)-2-oxo-2,3-dihydro-1H-indol-3-yl]-2-(4-ethylpiperazin-1-yl)propionamide 1) Under a stream of nitrogen, 520 mg of PCP are placed in 12 ml of anhydrous dichloromethane cooled in an ice bath, followed by slow addition of 430 mg of the acid of Preparation 1. The reaction mixture is left to act at 0° C. for 10 minutes and then at room temperature for 3 hours.

2) Separately, 300 mg of the product from Preparation 2 is suspended in 12 ml of dichloromethane under a stream of nitrogen, followed by addition of 0.3 ml of pyridine. The mixture is cooled in an Ice bath. The solution prepared in 1) is added dropwise and the mixture is stirred at room temperature for one hour.

The reaction mixture is poured into water and extracted with ethyl acetate. The organic phase is washed with saturated $NaHCO_3$ solution, dried over $Na_2SO_4$, filtered and evaporated under vacuum. 500 mg of an orange-coloured solid are obtained, which product is purified on a column by flash chromatography using 1/1 ethyl acetate/methanol as eluent, to obtain the title product.

m.p.=137-138° C.; $[\alpha_D]$=+217°, c=0.1064 wt % in MeOH;

NMR: δ (ppm, DMSO-$d_6$): 0.09 (m, 3H), 1.08 (m, 3H), 2.24-2.45 (m, 6H) 2.47-2.68 (m, **), 3.18-3.33 (m, *), 6.92 (m, 1H), 7.01 (s, 1H), 7.19 (m, 1H), 7.21-7.28 (m, 1H), 7.50 (bs, 1H), 7.65 (d, J=8.8 Hz, 1H), 8.02 (s, 1H), 8.61 (s, 0.4H****), 8.73 (s, 0.6H), 10.64 (s, 0.6H), 10.71 (s, 0.4H***).

LC/MS: (M+H)⁺=m/z 501 amu; rt=4.9 minutes

EXAMPLE 3

(+)-N-[4,6-Dichloro-3-(benzofuran-5-yl)-2-oxo-2,3-dihydro-1H-indol-3-yl]-2-(4-ethyl-3-methylpiperazin-1-yl)acetamide The process is performed as described for Example 1, but using 2-methyl-N-ethylpiperazine instead of 2,6-dimethyl-N-ethylpiperazine, to give the title compound.

The compounds according to the invention underwent in vivo studies.

In Vivo Test

Male Crl CD BR rats (Charles River, Italy) weighing 150-175 g were housed in a chamber at regulated temperature (22±1° C.) and humidity (55±10%) and with a 12-hour lightness-darkness cycle, for at least 7 days before their use. Feed and water were available ad libitum. The feed was removed 18 hours before sacrificing the animals. The rats were sacrificed by cervical dislocation, and the stomach was removed surgically, opened along the shorter curvature and placed in a Krebs solution (of composition (mM): 118.4 NaCl; 4.7 KCl; 2.5 $CaCl_2$; 3.7 $NaH_2PO_4$; 1.2 $MgSO_4$; 25 $NaHCO_3$; 5.6 glucose). The animals were cared for and sacrificed according to the Sanofi-Aventis international code of ethics and the international principles governing the care and treatment of laboratory animals (EEC Directive 86/609, DJL358, 1, 12 Dec. 1987). Strips of approximately 1 cm (5 mm wide) of gastric fundus were cut out along the longitudinal axis and suspended in 20 ml of bath filled with the Krebs solution at 37° C. and aerated with a 95% $O_2$-5% $CO_2$ gas mixture. The strips were maintained at a resting load of 1 g and, after washing, 10 μM of choline (acetylcholine precursor) and 10 μM of indomethacin (prostaglandin synthetase inhibitor) were added to the medium, to reduce the spontaneous phasic contractions (Depoortere et al., *Eur. J. Pharmacol.* 515, 1-3, 160-168, 2003; Dass et al., *Neurosciences* 120, 443-453, 2003). Isotonic contractions were initiated by stimulation with an electric field. Two platinum wire electrodes were placed at the surface and at the bottom of the organ bath, and the electric-field stimulation was performed with a Power Lab stimulator (AD Instruments Pty Ltd, Castle Hill, Australia) coupled to a multiplex pulse propeller (Ugo Basile, Varese, Italy) (Fukuda et al., *Scand. J. Gastroenterol,* 12, 1209-1214, 2004). The supramaximal stimulation was applied to create maximum contractions (20 Hz, pulse width: 2 milliseconds; 5 volts; batch trains every 2 minutes, 150 mA). Next, the current was reduced to obtain a submaximal stimulation (50% reduction of the maximum contractile response). The contractions were recorded by computer with a data recording and analysis system (Power Lab, Chart 5) connected to isotonic transducers (Ugo Basile, Varese, Italy) via preamplifiers (Octal Bridge Amp). After stabilization, concentration-response cumulative curves for ghrelin (0.1 nM-1 μM) were plotted, with and without incubation (contact time: 30 minutes) of the antagonist molecules. Supramaximal electric-field stimulation was used for each strip as reference (100%) to classify the responses per test substance. The agonist concentration producing 50% of the maximum effect ($EC_{50}$) was calculated using a four-parameter logistic model according to Ratkovsky and Reedy (*Biometrics,* 42, 575-582, 1986), with adjustment by non-linear regression using the Levenberg-Marquard algorithm in the Everstat software. The pKb values for the antagonists were calculated according to the Cheng-Prusoff equation (Kenakin et al., Competitive Antagonism, *Pharmacologic Analysis of Drug-Receptor Interaction,* 3rd edition, 331-373, Philadelphia, New York; Raven: Lippincott, 1997).

The compounds of formula (I) show antagonist activity towards the ghrelin receptor with $IC_{50}$ values ranging from $5 \times 10^{-8}$M and $1 \times 10^{-9}$M.

For example, the compound of Example No. 2 has an $IC_{50}$ value of $1.2 \times 10^{-8}$M.

The compounds of formula (I) demonstrated advantageous pharmacological properties for the development of a medicament, in particular medicaments for preventing or treating any pathology in which the ghrelin receptor is involved.

Thus, according to another of its aspects, a subject of the invention is medicaments comprising a compound of formula (I) or an addition salt thereof with a pharmaceutically acceptable acid.

Thus, the compounds according to the invention may be used, for man and animals, in the treatment or prevention of various ghrelin-dependent complaints. Thus, the compounds according to the invention may be used as anorexic agents, for regulating the appetite, the taking of meals and their frequency, and also, in the long-term, the weight, especially weight gain following diets or therapeutic regimens. The compounds according to the invention are thus particularly useful for preventing or treating obesity, appetite disorders, diabetes, excess weight and/or the effects thereof.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt thereof, and also at least one pharmaceutically acceptable excipient.

The said excipients are chosen, according to the pharmaceutical form and the desired mode of administration from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof may be administered in unit administration form, as a mixture with standard pharmaceutical excipients, to animals and human beings, for the prophylaxis or treatment of the above disorders or diseases.

The appropriate unit administration forms include oral-route forms such as tablets, soft or hard gel capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---:|
| Compound according to the invention | 50.0 mg |
| Mannitol | 223.75 mg |
| Sodium crosscarmellose | 6.0 mg |
| Corn starch | 15.0 mg |
| Hydroxypropylmethylcellulose | 2.25 mg |
| Magnesium stearate | 3.0 mg |

Via the oral route, the close of active principle administered per day may be from 0.1 to 100 mg/kg in one or more dosage intakes. Via the parenteral route, it may be from 0.01 to 10 mg/kg/day There may be particular oases in which higher or lower dosages are appropriate; such dosages do not depart from the scope of the invention. According to the usual practice, the dosage that is appropriate to each patient is determined by the practitioner according to the mode of administration, and the weight and response of the said patient.

Possible Combinations

The present invention also relates to combinations of one or more compound(s) according to the invention of general formula (I) with one or more active ingredient(s).

As active ingredient(s) that is (are) suitable for the said combinations, mention may be made especially of anti-obesity and antidiabetic agents, and also rimonabant, metformin or sulfonylureas.

According to another of its aspects, the present invention also relates to a method for treating the pathologies indicated above, which comprises the administration to a patient of an effective dose of a compound according to the invention, or of a pharmaceutically acceptable salt thereof.

According to another of its aspects, the present invention also relates to a compound of formula (I), or a pharmaceutically acceptable salt thereof, for treating the pathologies indicated above.

The invention claimed is:

1. A compound selected from the group consisting of:
   (+)-N-[4,6-dichloro-3-(benzofuran-5-yl)-2-oxo-2,3-dihydro-1H-indol-3-yl]-2-(4-ethyl-3-méthyl-piperazin-1-yl)acetamide;
   (+)-N-[4,6-dichloro-3-(benzofuran-5-yl)-2-oxo-2,3-dihydro-1H-indol-3-yl]-2-(4-ethylpiperazin-1-yl)propionamide; and
   (+)-N-[4,6-dichloro-3-(benzofuran-5-yl)-2-oxo-2,3-dihydro-1H-indol-3-yl]-2-(4-ethyl-3,5-dimethyl-piperazin-1-yl)acetamide,
   or a pharmaceutically acceptable salt thereof.

2. The compound of claim 1, wherein the pharmaceutically acceptable salt thereof is in the form of a base-addition salt.

3. The compound of claim 1, wherein the pharmaceutically acceptable salt thereof is in the form of an acid-addition salt.

4. A pharmaceutical composition, comprising:
   a compound of claim 1, or a pharmaceutically acceptable salt thereof; and
   a pharmaceutically acceptable excipient.

5. The pharmaceutical composition of claim 4 wherein the compound is in the form of a pharmaceutically acceptable acid addition salt.

6. A method of suppressing appetite in a human, comprising administering to the human a compound of claim 1, or a pharmaceutically acceptable salt thereof.

7. The method of claim 6, further comprising administering an anti-obesity agent.

8. The method of claim 7, wherein the anti-obesity agent is rimonabant.

9. A combination comprising the compound of claim 1 with one or more active agents selected from the group consisting of an anti-obesity agent and an anti-diabetic agent.

10. The combination of claim 9 wherein the anti-diabetic agent is metformin or sulfonylurea.

* * * * *